United States Patent [19]

Kukes et al.

[11] Patent Number: 4,659,688

[45] Date of Patent: Apr. 21, 1987

[54] MIXED METAL ORTHOPHOSPHATES

[75] Inventors: Simon G. Kukes; Gerhard P. Nowack; Robert L. Banks, all of Bartlesville, Okla.

[73] Assignee: Phillips Petroleum Company, Bartlesville, Okla.

[21] Appl. No.: 858,973

[22] Filed: May 2, 1986

Related U.S. Application Data

[62] Division of Ser. No. 788,297, Oct. 17, 1985, Pat. No. 4,613,719.

[51] Int. Cl.$^4$ .......................... B01J 27/18; C07C 2/02
[52] U.S. Cl. ..................................... 502/208; 585/528
[58] Field of Search ......................... 502/208

[56] References Cited

U.S. PATENT DOCUMENTS

| | | | |
|---|---|---|---|
| 2,189,655 | 2/1940 | Ruthruff | 585/528 |
| 2,414,206 | 1/1947 | Layng | 502/208 |
| 2,494,510 | 1/1950 | Hughes et al. | 585/528 |
| 3,130,147 | 4/1964 | Dwyer et al. | 502/208 |
| 4,507,402 | 3/1985 | Kukes | 502/208 |

*Primary Examiner*—P. E. Konopka
*Attorney, Agent, or Firm*—K. K. Brandes

[57] ABSTRACT

Catalyst composition comprising chemically bound copper, phosphorus and oxygen used for oligomerizing olefins to $C_5$–$C_{12}$ hydrocarbons. The preferred catalyst composition comprises a mixture of copper(II) orthophosphate, zirconium orthophosphate and aluminum orthophosphate, preferably formed by coprecipitation.

9 Claims, No Drawings

MIXED METAL ORTHOPHOSPHATES

This application is a division of our pending application Ser. No. 788,297, filed Oct. 17, 1985, now allowed U.S. Pat. No. 4,613,719.

BACKGROUND OF THE INVENTION

In one aspect, this invention relates to a process for converting lower olefins to higher hydrocarbons, which are useful as liquid fuels. In another aspect, this invention relates to the use of catalyst compositions comprising copper and the phosphate group for the oligomerization of olefins. In yet another aspect, a novel copper phosphate containing catalyst composition is provided.

The use of catalyst compositions, which comprise chemically bound copper, phosphorus and oxygen, for converting gaseous olefins to gasoline-type hydrocarbons is well known and has been disclosed in the patent literature, e.g., in U.S. Pat. Nos. 2,189,655 and 2,494,510. However, there is an ever present need to develop more efficient processes and more effective catalyst compositions than those presently known.

SUMMARY OF THE INVENTION

It is an object of this invention to provide a new, efficient process for converting olefins having from 2–4 carbon atoms per molecule, preferably α-olefins, to a product comprising hydrocarbons having from 5–12 carbon atoms per molecule. It is another object of this invention to employ copper and phosphate containing catalyst compositions in the process for oligomerizing olefins having 2–4 carbon atoms per molecule to hydrocarbons having 5–12 carbon atoms per molecule. It is a further object of this invention to convert propylene and/or 1-butene to hydrocarbons having 5–12 carbon atoms per molecule. It is still a further object of this invention, to provide a new, efficient catalyst composition. Other objects and advantages will be apparent from the detailed description and the appended claims.

In accordance with this invention, a process for oligomerizing olefins comprises the step of substantially simultaneously contacting (a) a feed stream which contains at least one olefin having from 2 to 4 carbon atoms per molecule, (b) a free hydrogen containing gas and (c) a solid catalyst composition comprising at least one compound containing copper, phosphorus and oxygen, wherein said contacting is carried out under such reaction conditions as to obtain a reaction product comprising at least one hydrocarbon having from 5 to 12 carbon atoms per molecule.

In one embodiment of this invention, feed stream (a) comprises α-olefins. In another embodiment, feed stream (a) comprises propylene. In yet another embodiment of this invention, feed stream (a) comprises 1-butene. In a further, presently preferred embodiment, catalyst composition (c) comprises at least one compound containing chemically bound copper, zirconium, aluminum, phosphorus and oxygen. In a still further embodiment, formed hydrocarbons having from 5 to 12 carbon atoms per molecule, which are useful as liquid fuels (such as for combustion engines), are separated from the formed reaction product.

In still another embodiment of this invention, there is provided a composition of matter comprising a mixture of copper(II) orthophosphate, zirconium orthophosphate and aluminum orthophosphate, preferably a coprecipitated mixture of copper(II) orthophosphate, zirconium orthophosphate and aluminum orthophosphate.

DETAILED DESCRIPTION OF THE INVENTION

Any feed stream which contains at least one olefin having 2–4 carbon atoms per molecule can be employed. Examples of suitable feed olefins are ethylene, propylene, 1-butene, 2-butene and 2-methyl-propylene. Presently preferred are propylene and 1-butene. The olefin feed stream can contain inert gases such as nitrogen and helium or gaseous paraffins such as methane and ethane.

The second process ingredient, a free hydrogen containing gas, can be introduced as a separate feed stream into a reactor (where the at least partial conversion of olefins to $C_5$–$C_{12}$ hydrocarbons occurs). In this case, at least partial mixing of the hydrogen stream with the olefin feed stream, during or prior to contacting with catalyst composition (c), is necessary to result in a reaction producing $C_5$–$C_{12}$ hydrocarbons. Or the hydrogen containing gas stream can be premixed with the olefin feed stream prior to entry into the reactor. The hydrogen containing gas stream can be substantially pure molecular hydrogen, or it can be a mixture of $H_2$ with other gases such as $N_2$, CO, $CO_2$, helium or other inert gases, gaseous paraffins, and the like.

The catalyst composition employed in the process of this invention comprises at least one compound containing chemically bound copper, phosphorus and oxygen, for example $Cu_3(PO_4)_2$, $CuHPO_4$, $Cu_3PO_4$, $Cu_2P_2O_7$ (copper(II) pyrophosphate), $Cu(PO_3)_2$ (copper(II) poly- and metaphosphates), $Cu_2PO_4(OH)$, $Cu_3(PO_3)_2$ (copper(II) phosphite), $Cu_3(PO_4)_2$-$Zr_3(PO_4)_2$, $Cu_2P_2O_7$-$ZrP_2O_7$, $Cu_3(PO_4)_2$-$AlPO_4$, $Cu_2PO_7$-$AlPO_4$, $Cu_3(PO_4)_2$-$Zr_3(PO_4)_2$-$AlPO_4$. Preferably phosphorus is pentavalent. Presently preferred is a mixture of $Cu_3(PO_4)_2$, $Zr_3(PO_4)_4$ and $AlPO_4$.

The preferred mixed Cu-Zr-Al orthophosphate containing composition of matter of this invention is preferably formed by coprecipitation from an aqueous solution of compounds that contain $Cu^{+2}$ ions, $Zr^{+4}$ or $ZrO^{+2}$ ions, and $Al^{+3}$ or $Al(OH)^{+2}$ or $[Al(OH)_2]^{+1}$ ions by addition of $H_3PO_4$ or at least one ionic compound containing $PO_4^{-3}$ or $HPO_4^{-2}$ or $H_2PO_4^{-}$ ions. Subsequently, the coprecipitated orthophosphate is dried and then calcined, preferably at a temperature in the range of from about 400° C. to about 600° C., for a time period varying from about 1 to about 6 hours, either in an oxidizing gas atmosphere (such as air) or in an inert gas (such as $N_2$, He, Ar). Suitable compounds that can be used in the above-described coprecipitation process include $CuSO_4$, $Cu(NO_3)_2$, $CuCl_2$ and the like; $Zr(NO_3)_4$, $ZrO(NO_3)_2$, $ZrOCl_2$ and the like; $AlCl_3$, $Al(NO_3)_3$, $Al_2(SO_4)_3$, $AlOHCl_2$ and the like; $H_3PO_4$, $NaH_2PO_4$, $NH_4H_2PO_4$, $(NH_4)_2HPO_4$, $(NH_4)_3PO_4$ and the like.

Optionally, the above-described coprecipitation of Cu-Zr-Al orthophosphate can be carried out from an aqueous solution containing at least one finely dispersed inorganic refractory material therein, thus producing a mixture of copper(II) orthophosphate, zirconium orthophosphate, aluminum orthophosphate and said at least one inorganic refractory material. Non-limiting examples of such inorganic refractory materials are alumina, silica, aluminosilicates (e.g., zeolites), titania, zirconia and magnesia, preferably alumina. When such a refractory material is present, the amount of it in the entire mixture generally is about 1–90 weight percent.

Even though coprecipitation is the presently preferred preparation method of mixed Cu-Zr-Al orthophosphate (i.e., a mixture of copper(II) orthophosphate, zirconium orthophosphate and aluminum orthophosphate), it is within the scope of this invention (yet presently less preferred) to employ other methods of preparation. For example, copper(II) orthophosphate, zirconium orthophosphate and, aluminum orthophosphate can be mixed and then be at least partially fused. Or copper(II) orthophosphate can be impregnated with a zirconium compound and an aluminum compound, and the thus impregnated copper(II) orthophosphate can be treated with phosphoric acid or a solution of an ionic phosphate.

The weight ratio of the sum of metals (copper, zirconium, aluminum) to phosphorus in the catalyst compositions employed in this invention is generally in the range of from about 1.5:1 to about 3:1. When Zr is present, the atomic ratio of Zr to Cu is generally in the range of from about 0.5:1 to about 5:1. When Al is also present, the atomic ratio of Al to Cu is generally in the range of from about 0.5:1 to about 5:1. The surface area (determined by mercury porosimetry, described in Example II) generally is in the range of from about 20 to about 300 m$^2$/g.

In the oligomerization process of this invention, the simultaneous contacting of at least one $C_2$–$C_4$ olefin, a free hydrogen containing gas and the catalyst composition can be carried out under any suitable reaction conditions that result in the at least partial conversion of the said olefin to $C_5$–$C_{12}$ hydrocarbons. The reaction can be carried out as a batch process or as a continuous process. In a batch process, the olefin, a free hydrogen containing gas and catalyst composition can be added in any order to a reaction vessel, which is preferably equipped with mixing/agitating means so as to ensure simultaneous contact of the trace process ingredients. In a continuous process, which is presently preferred, one or more gas streams comprising at least one $C_2$–$C_4$ olefin and a free hydrogen containing gas are passed through a fixed bed containing one of the copper- and phosphate-containing catalyst compositions (optionally admixed with essentially inert refractory solids such as alumina or silica), under such reaction conditions as to produce $C_5$–$C_{12}$ hydrocarbons.

Any suitable mole ratio of olefin(s) to free hydrogen can be employed in the oligomerization process of this invention. Generally, the olefin to hydrogen mole ratio is in the range of from about 1:10 to about 10:1, preferably from about 1:3 to about 3:1.

Heating of the process ingredients (a), (b) and (c) is generally required to accomplish a conversion of olefins to $C_5$–$C_{12}$ hydrocarbons. Any suitable temperature that will cause and maintain a controllable reaction can be employed. Any feasible heating means can be utilized. It is within the scope of this invention to preheat one or more of the process ingredients before they are introduced into a reactor, which is heated to maintain a suitable temperature. Generally the reaction temperature ranges from about 100° F. to about 1,000° F., more preferably from about 300° F. to about 800° F.

The reaction pressure can vary from subatmospheric pressure to elevated pressure such as up to 500 psig. The selection of the reaction pressure will greatly depend on the reaction temperature, the volatility of process ingredients and products, and the specific reactor design. Generally, the pressure is approximately atmospheric (about 1 atm, 0 psig).

In a batch process, the reaction time, i.e., the time of intimate, simultaneous contact of the process ingredients (a), (b) and (c), can vary from about 20 minutes to about 20 hours and will preferably be in the range of about 1 to about 5 hours. The actual reaction time will greatly depend on the relative amounts of process ingredients, the selection of an effective, yet safe, reaction temperature, the reaction pressure, and the extent of mixing and agitation during the reaction. In a continuous process, the gas hourly space velocity of the olefin feed is generally in the range of from about 100 to about 10,000 cc olefin/cc catalyst composition/hour, preferably from about 400 to about 2,000 cc/cc/hr.

The formed reaction products, which comprise at least one $C_5$–$C_{12}$ hydrocarbon, can be separated from the reaction mixture by any suitable separation means such as fractional distillation, or crystallization, or extraction with a suitable solvent (e.g., a liquid paraffin such as n-hexane) plus subsequent evaporation of the solvent. Unreacted process ingredients can be separated in a similar manner and can be recycled to the reaction zone with added fresh ingredients. The produced $C_5$–$C_{12}$ hydrocarbons can be used as motor fuels.

The following examples are presented to further illustrate this invention without unduly limiting the scope of the invention.

EXAMPLE I

This example illustrates the preparation of copper phosphate catalysts that were employed in the oligomerization of propylene and 1-butene.

Catalyst A was prepared substantially in accordance with the procedure described in U.S. Pat. No. 2,189,655. 122.5 grams of sodium pyrophosphate (lot KHKR, Mallinckrodt, Inc., St. Louis, Mo.) were dissolved in 1375 cc of deionized water. A second solution was made by dissolving 125 grams of $CuSO_4.5H_2O$ (Lot KTSY; Mallinckrodt, Inc.) in 2500 cc of deionized water. The two solutions were mixed with stirring for 30 minutes at 40° C. The formed precipitate of copper pyrophosphate was recovered by filtration, washed with 4 liters of deionized water and dried in an oven for 100 hours at 160° C.

Catalyst B was copper-zirconium-aluminum orthophosphate prepared as follows. A first solution was prepared by dissolving 48.3 g (0.2 mole) of $AlCl_3.6H_2O$ (Lot KPRP, Mallinckrodt, Inc.), 50.0 g (0.2 mole) of $ZrOCl_2.4H_2O$ (Lot 061083; Alfa Products) and 48.3 g (0.2 mole) of $Cu(NO_3)_2.3H_2O$ in 600 cc of distilled water. The formed solution (pH: 0.25) was stirred at room temperature until it was clear and then heated at 65° C. for 30 minutes. Aqueous ammonia was added to adjust the pH to about 3. A second solution was prepared by dissolving 71.3 of $(NH_4)_2HPO_4$ in 300 cc distilled water. This second solution (pH: 8.1) was stirred at room temperature until it was clear and then heated at 65° C. for 30 minutes. The first solution was added to the second solution, and the formed gel was manually stirred with a spatula for several minutes. The gel slurry was filtered, and the filter cake was dried. The dried precipitate was reslurried in 1 liter of water and refiltered. The Cu-Zr-Al-$PO_4$ filter cake was dried overnight at about 120° C. and calcined for 4 hours at 500° C.

The calcined Catalyst B was ground and sieved, and a 14/40 mesh portion was collected. Catalyst B contained 8.25 weight-% Cu, 20.62 weight-% Zr, 7.43 weight-% Al and, 16.56 weight-% P and oxygen as the balance. The average surface area of two separately prepared samples of Catalyst B was about 148 m²/g; the pore volume was about 0.94 cc/g; and the average pore diameter was about 255 Å. All surface/pore measurements were carried out by mercury porosimetry (mercury intrusion at a pressure ranging from an initial pressure of 0 psig to a final pressure of about 15,000 psig.

EXAMPLE II

This example illustrates the oligomerization of propylene and n-butene, with and without added hydrogen gas, over Catalysts A and B.

All runs were made by passing a propylene or 1-butene feed through a vertical tubular quartz reactor (1 cm in diameter and 25 cm in length) positioned in a temperature-controlled electric furnace. In each run, the reactor contained a bed of the designated catalyst. Thermocouples were positioned in the catalyst bed to monitor the reaction temperature. Prior to each run, the catalyst was activated by heating in air at 500° C. for about 30 minutes and then in nitrogen at 500° C. for about 15 minutes. The propylene and 1-butene feeds were of polymerization grade as sold by Phillips Petroleum Company of Bartlesville, Okla. The propylene or 1-butene feed was pretreated with activated Alcoa H151 alumina and activated magnesia prior to the oligomerization. The feed (14–15 psia) was passed downwardly through the vertically oriented tubular reactor.

Reaction product analyses were made by gas-liquid chromatography (GLC) employing a Hewlett-Packard model 5880A chromatograph having a ⅛ inch by 20 ft. column packed with 19% BMEE+1% squalene on 60/80 Chrom P. Analyses were carried out isothermally at a temperature of about 30° to 40° C. with a helium carrier gas flow rate of about 20 mL/min. Hydrogen gas was introduced in small amounts during the oligomerization reaction at various time intervals. Pertinent process parameters and product compositions are summarized in Table I.

bon production was greatest when Catalyst B was employed. Thus Catalyst B (Cu-Zr-Al-PO$_4$) is presently preferred over Catalyst A (copper pyrophosphate) in the instant invention.

Reasonable variations and modifications can be made in this invention without departing from the spirit and scope thereof.

We claim:

1. A composition of matter comprising a mixture of copper(II) orthophosphate, zirconium orthophosphate and aluminum orthophosphate, wherein the atomic ratio of Al contained in said aluminum orthophosphate to Cu contained in said copper(II) orthophosphate is in the range of from about 0.5:1 to about 5:1 and wherein the atomic ratio of Zr contained in said zirconium orthophosphate to Cu contained in said copper (II) orthophosphate is in the range of from about 0.5:1 to about 5:1.

2. A composition of matter in accordance with claim 1 wherein said mixture of copper(II) orthophosphate, zirconium orthophosphate and aluminum orthophosphate has been formed by coprecipitation.

3. A composition of matter in accordance with claim 2 further comprising at least one inorganic refractory material.

4. A composition of matter in accordance with claim 3, wherein said at least one inorganic refractory material is alumina.

5. A composition of matter in accordance with claim 1 having a weight ratio of (Cu+Zr+Al) to P in the range of from about 1.5:1 to about 3:1.

6. A composition of matter in accordance with claim 2 having a surface area, determined by mercury porosimetry, in the range of from about 20 to about 300 m²/g.

7. A composition of matter in accordance with claim 2, wherein said composition of matter has been calcined in an oxidizing gas at a temperature in the range of from about 400° C. to about 600° C.

8. A composition of matter in accordance with claim

TABLE I

| Run | Feed | Catalyst | Reaction Temp. (°C.) | H$_2$ Added | Mole-% in Reactor Effluent | | | | |
|---|---|---|---|---|---|---|---|---|---|
| | | | | | Ethylene | Propane | Propylene | Butenes | C$_5$+ Hydrocarbons |
| 1 (Control) | Propylene | A | 250 | No | 0.01 | 0.25 | 99.68 | 0.01 | 0.03 |
| 2 (Invention) | Propylene | A | 250 | Yes | 0.60 | 0.26 | 95.68 | — | 0.24 |
| 3 (Control) | Propylene | B | 250 | No | 0.01 | 0.26 | 99.70 | 0.01 | 0.00 |
| 4 (Invention) | Propylene | B | 250 | Yes | 0.22 | 0.33 | 93.04 | 0.04 | 5.07 |
| 5 (Control) | Propylene | B | 250 | No | 0.01 | 0.28 | 99.68 | — | 0.01 |
| 6 (Invention) | Propylene | B | 250 | Yes | 0.01 | 0.29 | 99.05 | 0.01 | 0.62 |
| 7 (Control) | 1-Butene | B | 320 | No | 0.01 | — | 0.23 | 95.90 | 3.76 |
| 8 (Invention) | 1-Butene | B | 319 | Yes | — | — | 0.14 | 85.76 | 13.7 |
| 9 (Control) | 1-Butene | B | 267 | No | — | — | — | 95.2 | 4.01 |
| 10 (Invention) | 1-Butene | B | 266 | Yes | — | — | 0.10 | 91.9 | 7.33 |

Data in Table I clearly show that the addition of hydrogen gas to the reactor during oligomerization runs had a beneficial effect on the formation of the desirable fractions of hydrocarbons having 5 or more carbon atoms per molecule. This effect was observed for the oligomerization of propylene as well as of 1-butene, over copper pyrophosphate (Catalyst A) as well as over Cu-Zr-Al-PO$_4$ (Catalyst B). The C$_5$+ hydrocar- 2, wherein said composition of matter has been calcined in an inert gas at a temperature in the range of from about 400° C. to about 600° C.

9. A composition of matter in accordance with claim 4, wherein the amount of alumina in said composition of matter is in the range of from about 1 to about 90 weight percent.

* * * * *